US006361955B1

United States Patent
Hösel et al.

(10) Patent No.: US 6,361,955 B1
(45) Date of Patent: Mar. 26, 2002

(54) IMMUNOLOGICAL PROCESS FOR PSA DETERMINATION

(75) Inventors: Wolfgang Hösel, Tutzing (DE); Jochen Peter, Research Triangle Park, NC (US); Carlo Unverzagt, Munich (DE)

(73) Assignee: Roche Diagnostics GmbH (DE)

(*) Notice: Subject to any disclaimer, the term of this patent is extended or adjusted under 35 U.S.C. 154(b) by 0 days.

(21) Appl. No.: 09/283,955

(22) Filed: Apr. 1, 1999

(30) Foreign Application Priority Data

Apr. 3, 1998 (DE) .......................................... 198 14 915

(51) Int. Cl.$^7$ ...................... G01N 33/53; G01N 33/573; G01N 33/536; C12Q 1/37; C07K 1/14
(52) U.S. Cl. ........................... 435/7.1; 435/7.4; 435/23; 436/64; 436/536; 530/412
(58) Field of Search ............................... 435/4, 7.1, 7.2, 435/7.21, 7.23, 7.4, 23; 436/501, 536, 8, 15, 64; 530/395, 350, 412, 413

(56) References Cited

FOREIGN PATENT DOCUMENTS

| EP | 0 635 575 A1 | 1/1995 |
| EP | 0 789 032 A2 | 8/1997 |
| WO | WO 92/01936 | 2/1992 |
| WO | WO 97/12245 | 4/1997 |
| WO | WO 98/10292 | 3/1998 |

OTHER PUBLICATIONS

Becker, et al., "Individual prostate–specific antigen (PSA) forms as prostate tumor markers,"Clinica Chimica Acta 257:117–132 (1997).
Blase, et al., "Reply to the Editor,"Clinical Chemistry 44:192–193 (1998).
Bunting, Peter S., "A Guide to the Interpretation of Serum Prostate Specific Antigen Levels,"Clinical Biochemistry 28:221–241 (1995).
Chen, et al., "Purification and Characterization of Prostate–Specific Antigen (PSA) Complexed to Alpha1–Antichymotrypsin: Potential Reference Material for International Standardization of PSA Immunoassays,"Clinical Chemistry 41:1273–1282 (1995).
Chu, T. Ming, "Prostate–Specific Antigen and Early Detection of Prostate Cancer,"Tumor Biology 18:123–134 (1997).
Huber, et al., "In Vivo and In Vivo Complex Formation of Prostate Specific Antigen With Alpha1–Chymotrypsin,"The Prostate 27:166–175 (1995).
J. Malm, et al., "Biochemistry of prostate specific antigen, PSA,"Scand J Clin Lab Invest 55:15–22 (1995).
McCormack, et al., "Molecular Forms Of Prostate–Specific Antigen And The Human Kallikrein Gene Family: A New Era,"Urology 45:729–744 (1995).
Oesterling, Joseph E., "Prostate Specific Antigen: A Critical Assessment of the Most Useful Tumor Marker for Adenocarcinoma of the Prostate,"The Journal of Urology 145:907–923 (1991).
Tewari, et al., "Multiple Forms of Prostate Specific Antigen and the Influences of Immunoassay Design on their Measurement in Patient Serum,"Journal of Clinical Ligand Assay 18:186–196 (1995).
Tewari, et al., "Analytical Characteristics of Seminal Fluid PSA Differ from Those of Serum PSA,"Clinical Chemistry 44:191–192 (1998).
Zhou, et al., "Multiple Forms of Prostate–Specific Antigen in Serum: Differences in Immunorecognition by Monoclonal and Polyclonal Assays,"Clinical Chemistry 39:2483–2491 (1993).
Cooperman, B.S. et al. Antichymotrypsin interaction with chymotrypsin. J. Biol. Chem. 268: 23616–23625, Nov. 1993.*
Peter, J. et al. Analysis of free prostate–specific antigen (PSA) after chemical release from the complex with alpha1–antichymotrypsin (PSA–ACT). Clin. Chem. 46(4): 474–482, 2000.*
Sigma Chemical Company, p. 415 and p. 96, 1994.*

* cited by examiner

Primary Examiner—Anthony C. Caputa
Assistant Examiner—Anne L. Holleran
(74) Attorney, Agent, or Firm—Marilyn L. Amick; Roche Diagnostics Corporation

(57) ABSTRACT

The invention concerns an immunological process for the determination of prostate-specific antigen (PSA), particularly for the determination of free PSA, the total concentration of PSA and the concentration of PSA-serpin complexes by incubation of the sample with at least one antibody specifically binding to free PSA but not to complex PSA. The process is characterized in that especially before the determination of the total PSA concentration a nucleophile containing amine is added to the sample. Furthermore, the invention concerns the use of amine-containing nucleophiles for the production of free PSA as well as a procedure for preparing free PSA from complex PSA by incubation of a sample containing complex PSA with a nucleophile containing amine.

12 Claims, 2 Drawing Sheets

IMMUNOLOGICAL PROCESS FOR PSA DETERMINATION

The present invention concerns an immunological process for the determination of prostate-specific antigen (PSA), in particular for the determination of free PSA, the total PSA level and the concentration of PSA-serpin complexes by incubation of the sample with at least one antibody specifically binding to free PSA but not binding to complex PSA. The process is characterized in that a nucleophile containing amine is added to the sample before the determination of the total PSA concentration. Furthermore, the invention concerns the use of amine-containing nucleophiles for the production of free PSA as well as a process for preparing free PSA from complex PSA by incubation of a sample containing complex PSA with an amine-containing nucleophile.

The prostate-specific antigen is a glycoprotein with a molecular weight of 29 kDa. It is built in the epithelial prostate cells and is a component of the seminal fluid. PSA has the enzymatic activity of a neutral serine protease.

The main function of PSA is the cleavage of the seminogelines I and II as well as of fibronectin which—as essential ejaculation components—block the sperm mobility. By the hydrolysis of these proteins PSA liquefies the semen coagulum and thus enables the sperm mobility.

The enzymatically active PSA is inactivated in the serum by various inhibitors. The so-called serpins (=serine protease inhibitors) belong to the most important inhibitors which inactivate PSA by forming covalent complexes. The main amount (60–95%) of the immunologically detectable PSA is bound in the serum to α1-antichymotrypsin (=ACT), which belongs to the serpins.

Further complexes can be formed with α1-antitrypsin and protein C inhibitor which are, however, in comparison to PSA-ACT, only of secondary importance in the serum.

In addition, PSA also forms a complex with a different type of protease inhibitor, i.e. the α2-macroglobulin (α2-M). Information on the complex concentration in the serum are different in the literature which is particularly due to the immunological inaccessibility of the PSA in this complex. The serum also contains enzymatically inactive free PSA which cannot form complexes. In the following "total PSA" means the sum of free PSA and serpin-complex PSA since the PSA complex with α2-M is not registered in any immunological determination performed until now. (Teware and Bluestein, J. Clin. Ligand Assay 1995, vol. 18, p. 186–196).

α1-antichymotrypsin is a glycoprotein with a molecular weight of approx. 60 kDa. As one of the main inhibitors in the acute phase ACT plays an important role in the control of inflammation. ACT also forms complexes with chymotrypsin, cathepsin G and glandular callicrein hK2. In human serum the molar ACT concentration is 10,000 times higher than that of PSA.

Due to the occurrence of different PSA forms the conditions for determination of the PSA concentration in human sera for the diagnosis of a prostate carcinoma or a benign disease are very complex. This fact evokes a number of diagnostic difficulties and reduces the value of this marker to a certain extent. Thus, it is known that some of the available assays for the determination of PSA give different values of free and complex PSA due to the specificity of the antibodies used thou et al., Clin. Chem. 1993, Vol. 39/12, p. 2483–2491; McCormack et al., Urology 1995, Vol. 45, p. 729–744; Tewari and Williams, Clin. Chem. 1998, Vol. 44, p. 191–192; Blase and Sokoloff, Clin. Chem. 1998, Vol. 44, p.192–193). In addition, an exact and uniform standardization is difficult because of the occurrence of the different forms mentioned (Chen et al., Clin. Chem. 1995, Vol. 41, p. 1273–1282).

The reliability of the PSA serum values as an indicator of a prostate carcinoma (PCa) up to a concentration of approx. 15 ng/ml is particularly problematic since such concentrations of total PSA can also result from the occurrence of a benign prostate hyperplasia (BPH). A prostate carcinoma screening by simple determination of the PSA value in the serum is not possible due to the lacking specificity in this concentration range; further investigations which are partly complex and painful (biopsy) must be performed to find out whether a PCa has occurred or not.

During the last years the determination of the ratio of free, i.e. uncomplexed PSA to complexed PSA or total PSA could improve the specificity to a certain extent (see e.g. WO 92/01936). It is, however, still clearly below a specificity value which would be necessary to avoid a larger number of unnecessary and time-/cost-intensive further examinations. The improvement of the specificity is based on the fact that in sera of patients with BPH the average ratio of free to complex PSA (PSAfree/PSAtotal) is higher than in sera of PCa patients.

For state of the art establishment of the PSAfree/PSAtotal ratio two different measurings must be performed. First of all the concentration of free PSA must be determined. If this test for free PSA is carried out in the sandwich format at least one of the two antibodies must be specific for free PSA and must not bind to complex PSA. Simultaneously, the total PSA concentration must be established in a second separate measurement. In this case the antibodies used in the sandwich test bind to free and complex PSA. Alternatively, the total concentration can also be determined by measuring the PSA-ACT concentration. In the WO 92/01936 such an antibody binding to free and complex PSA as well as an antibody specifically binding to ACT is used for the detection of the PSA-ACT concentration.

The total PSA amount can be achieved by adding the measuring value of the PSA-ACT complex and the measuring value of free PSA.

A big disadvantage of the state of the art process is that two different tests are performed which involve each at least two antibodies with a different specificity. The use of different reagents, e.g. antibodies, in several test procedures for the determination of a diagnostically relevant parameter very probably leads to problems when comparing tests of different manufacturers, particularly when such a complex diagnostic problem like that of PSA is regarded. In addition, the fault probability of the determination of reagents rises with the number of test systems used and reagents required. Furthermore, the provision of a large number of different, generally monoclonal antibodies is very cost- and time-intensive.

The task was therefore to develop an improved and simplified immunological process for the detection of PSA, in particular for the detection of free PSA, the total PSA concentration and the concentration of PSA-serpin complexes to overcome the state of the art disadvantages to a large extent.

The task is fulfilled with an improved immunological process for quantitative determination of PSA by incubation of the sample with at least one antibody binding specifically to free PSA but not to complex PSA, wherein an amine-containing nucleophile is added to the sample before the determination of the total PSA concentration. This procedure is preferably used for the quantitative determination of the concentration of free PSA, total PSA and of the PSA-serpin complexes.

The complex of PSA and serpins, in particular ACT, is stable and withstands drastic temperature and pH conditions (McCormack et al., Urology 1995, Vol. 45, p. 729–744). Surprisingly, it has been shown that the PSA-serpin complex can be cleaved by adding amine-containing nucleophilic reagents.

HPLC analyses have shown that the resulting PSA is stable. Surprisingly, this is also the case in the presence of serum, i.e. no new complexes are built. This can be recognized by the value of free PSA after the incubation under cleavage conditions which corresponds to the total PSA value before the cleavage. This result is surprising because free PSA in the serum actually should have been complexed again due to the very high excess of the protease inhibitors $\alpha$1-antichymotrypsin and ($\alpha$2-macroglobulin. This is at least the case when additional PSA is added to a human serum sample (Maim and Lilja, Scand. J. Clin. Invest. 1995 Vol.55, p. 15–22; Huber et al. The Prostate 1995, Vol. 27, p. 166–175).

Due to the practically irreversible cleavage of the PSA-serpin complex (in particular of the PSA-ACT complex) the possibility to determine the free PSA concentration in the untreated sample does exist. This is preferably carried out by a sandwich immunoassay where at least one of the antibodies specifically binds to free PSA but not to complex PSA. An amine-containing nucleophilic reagent is added to an identical parallel sample which leads to the cleavage of the serpin-complexed PSA (mainly PSA-ACT) and the release of the previously complexed PSA. Subsequently, the concentration of free PSA is determined in the same measuring procedure, i.e. by means of the same antibodies. The resulting value corresponds to the total PSA concentration. The synonyms "total concentration of PSA", "total PSA", "total level of PSA" and "$PSA_{total}$" in the state of the art all mean the amount of free PSA and PSA complexed with serpins.

By dividing the concentration of free PSA by that of total PSA one obtains the informative ratio $PSA_{free}/PSA_{total}$. By subtracting the value of $PSA_{free}$ from $PSA_{total}$ the concentration of PSA complexed with serpins can also be determined and subsequently the ratio $PSA_{free}$/PSA serpin complex and $PSA_{free}$/PSA-ACT can be determined too.

With a certain degree of probability this ratio indicates the occurrence of a BPH or a PCa. The higher this ratio the higher is the probability of the occurrence of a benign disease.

An appropriate procedure of the process according to the invention for the determination of free PSA and of the total PSA concentration includes the following steps: a) Incubation of a part of the sample with at least one antibody specifically binding to free PSA but not to complex PSA, b) determination of the concentration of free PSA, c) incubation of a part of the sample with an amine-containing nucleophilic reagent, d) incubation of the sample from step c) with an antibody according to step a), e) determination of the total PSA concentration in the sample according to step b), and f) determination of the ratio: free PSA to total PSA concentration using the values from step b) and e).

If the ratio PSAfree/PSA-serpin complex and PSAfree/PSA-ACT is to be established the following has to be done: as step f) the concentration of free PSA from step b) is subtracted from the total PSA concentration and as step g) the ratio of free PSA according to step b) and the PSA-serpin complex value and, respectively, the PSAfree/PSA-ACT value from step f) is built.

For a successful method procedure it is essential that the free PSA obtained by the cleavage according to the invention is immunologically reactive. This means that the epitopes recognized by the antibodies will be completely preserved even after the cleavage by amine-containing nucleophilic reagents. An important advantage of the process according to the invention is that for the determination of free and total PSA the same antibodies, i.e. antibodies of the same specificity can be used. The time- and cost-intensive development of antibodies with a different specificity as required in the state of the art processes can thus be avoided. The higher the number of different antibodies used the higher is the risk of unspecific interactions with sample components.

Since in the process according to the invention mostly only two different antibodies are used these interactions can be reduced considerably compared to the state of the art.

Heterogeneous and homogeneous test procedures are appropriate test formats for the process according to the invention. The conventional heterogeneous sandwich assay has proven to be particularly advantageous. Here, the analyte (in our case the PSA antigen and, in the state of the art processes also the PSA-ACT complex) is bound like a sandwich between a binding partner bound to a solid phase and a labeled binding partner there: the antibody). The labeling is detected according to measures known to the expert. Usual labelings are enzymes, luminescent substances, haptens such as digoxigenin, fluorescent and radioactive substances. Plastic tubes, microtiter plates, latex particles or magnetic beads can for example be used as the solid phase. A surface coated with streptavidin or avidin is used preferably. The antibody can be bound directly by adsorption to the solid phase or, preferably, indirectly. In the case of an indirect binding an antibody coupled with biotin binds to the solid phase coated with streptavidin or avidin.

PSA can also be detected by means of a competitive procedure. In this case a solid-phase bound complex is built by two binding partners specific for each other where the binding partner which is not directly bound to the solid phase is labeled. The analyte which is—depending on the test requirements—an antigen or an antibody dislodges the labeled binding partner according to its concentration from the complex. After the separation of the solid phase from the liquid phase the labeling is detected in one of the phases. For a PSA test with a competitive test procedure the solid-phase bound binding partner would for example be an antibody specific for free PSA. The other binding partner would, then, be labeled free PSA. Afterwards this labeled free PSA is dislodged by the free PSA in the sample depending on the concentration of free PSA.

The test formats and their procedures mentioned as well as the detection of the analytes are only presented as examples for illustration. The methods are known to the expert and need no further explanation here.

In all test formats at least one antibody specifically binding to free PSA but not to complex PSA must be used. The antibody can be monoclonal or polyclonal. The antibody preferred is, however monoclonal. Whole antibodies as well as fragments thereof such as Fab, F (ab)', F(ab)'$_2$ can be used. What is important is the specificity for free PSA which means that the antibody specific for free PSA may only react with uncomplexed PSA. Cross reactivities with complex PSA must not occur at all or only to such a negligible extent that they do not distort the test results. If further antibodies are necessary they can also be used as intact monoclonal or polyclonal antibodies or fragments thereof. The requirements for these further antibodies are that they must recognize free PSA. A cross reaction with complex PSA is, however, not critical.

According to the invention all biological fluids known to the expert can be used as samples. Body fluids such as whole blood, blood serum, blood plasma, sperm or urine are used preferably as samples.

According to the invention nucleophilic amine-containing reagents are used for the cleavage of the PSA-serpin complexes to which belong preferably amino alcohol like e.g. ethanolamine and diethanolamine. Ethanolamine is used particularly preferably. The PSA-ACT complexes are split by adding the nucleophilic amine-containing reagent to any sample containing PSA in a complex form. A reagent concentration of 0.05 to 2 M has proven to be appropriate. The concentration preferably used is 0.1 to 1 M. The preferable pH in the sample is between 9 and 11. The incubation temperature of the thus treated sample containing the nucleophilic amine-containing reagent is not critical. A temperature between 10 and 40° C., preferably between 20 and 30° C., particularly preferably of 25° C. has been proven to be appropriate. The incubation in general takes several hours. Since the free PSA formed by cleavage is stable incubation periods of 24 hours and more are possible for the process according to the invention. Therefore another subject matter of the invention is also a process for the production of free PSA by incubation of a sample containing complex PSA with a nucleophilic amine-containing reagent under the conditions mentioned before. Afterwards the resulting free PSA can for example be used for further diagnostic or scientific structure or function investigations.

A further subject matter of the invention is therefore the use of the free PSA produced according to the process in accordance with the invention for non-immunological investigations like e.g. mass spectrometry.

A further subject matter of the invention is the use of a nucleophilic amine-containing reagent, preferably of an amino alcohol and particularly preferably of ethanolamine for the production of free PSA.

The PSA produced according to the above process can also be used as a standard according to the invention. Such a standard can be used for the establishment of calibration curves in immunoassays for the quantitative detection of PSA.

A further subject matter of the invention is the use of a nucleophilic amine-containing reagent in an immunological process for the quantitative detection of PSA. Ethanolamine is used preferably.

A further subject matter of the invention is a reagent containing at least one nucleophilic amine-containing reagent, preferably ethanolamine for the use in an immunoassay to detect PSA as well as further components known to the expert such as buffers, salts and detergents. The reagent is preferably provided in liquid, aqueous form.

The invention is further described by the following examples.

Example 1

Cleavage of PSA-ACT With Amine-containing Nucleophiles

Commercially available substances of Scripps Laboratories, San Diego, Calif., USA: $PSA_{free}$ (lyophilized) catalogue No. P0714, PSA-ACT catalogue No. P0624. Both lyophilizates are each resuspended with bidistilled water, final concentration: 1 mg/ml. PBS buffer of Boehringer Mannheim GmbH Germany (ident. No. 2958686) is used as cleavage buffer. 2 μg PSA-ACT in 40 μl cleavage buffer are used per cleavage preparation. For cleavage of the PSA-ACT containing samples the amine-containing nucleophiles to be tested which are listed in table 1 are added to the sample and incubated at 25° C. After incubation the samples are separated by HPLC under the following conditions:

| Column: | Reversed Phase Column Poros R 1/H, 2.1 × 30 mm |
|---|---|
| Elution buffer A: | 0.1% trifluoroacetic acid |
| Elution buffer B: | 0.085% trifluoroacetic acid in acetonitrile/water 70/30 |
| Gradient: | 20% B in A from 0 to 2 min, linear rise up to 100% B within 11 min; 100% B for 2 min. |

The cleavage efficiency of the substances used is listed in table 1.

TABLE 1

Cleavage efficiency of the different amine-containing nucleophiles at 25° C.

| Amine-containing nucleophile | % cleavage after 65 h |
|---|---|
| 0.1 M ethanolamine, pH 9.0 | 28% |
| 0.5 M ethanolamine, pH 9.0 | 37% |
| 1 M ethanolamine, pH 9.0 | 61% |
| 0.1 M diethanolamine, pH 9.0 | 17% |
| 0.1 M ethylenediamine, pH 9.0 | 8% |
| 1 M TRIS, pH 9.0 | 14% |

It becomes clear that the highest cleavage efficiency is achieved with ethanolamine. FIGS. 1 and 2 show HPLC chromatogram examples of the PSA-ACT cleavage.

Example 2

Figure 1:
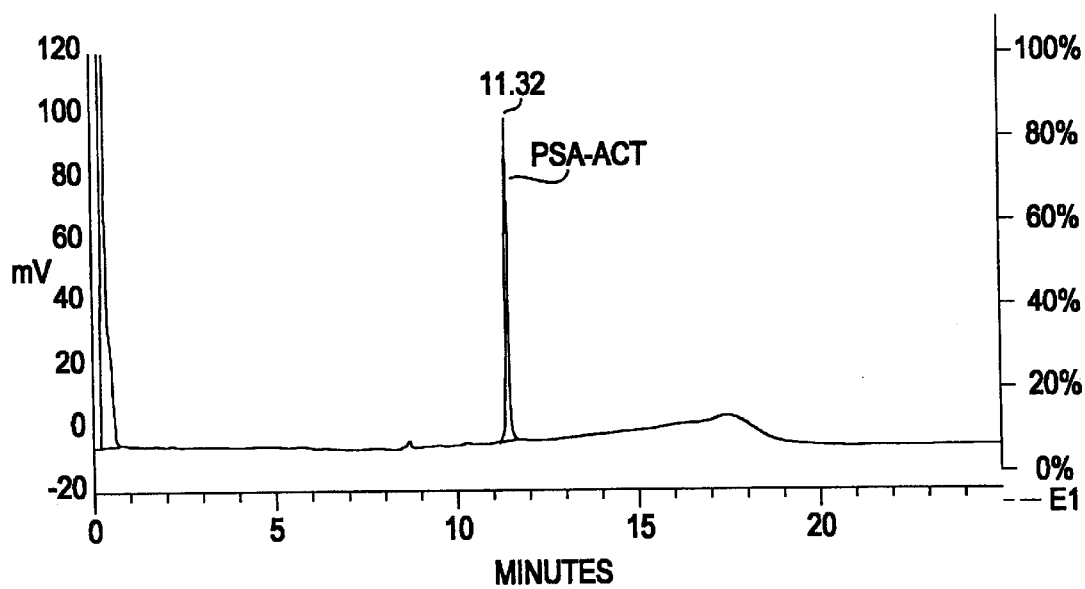
FIG. 1 shows an HPLC chromatogram of PSA-ACT in PBS buffer before the cleavage with ethanolamine.
Figure 2:
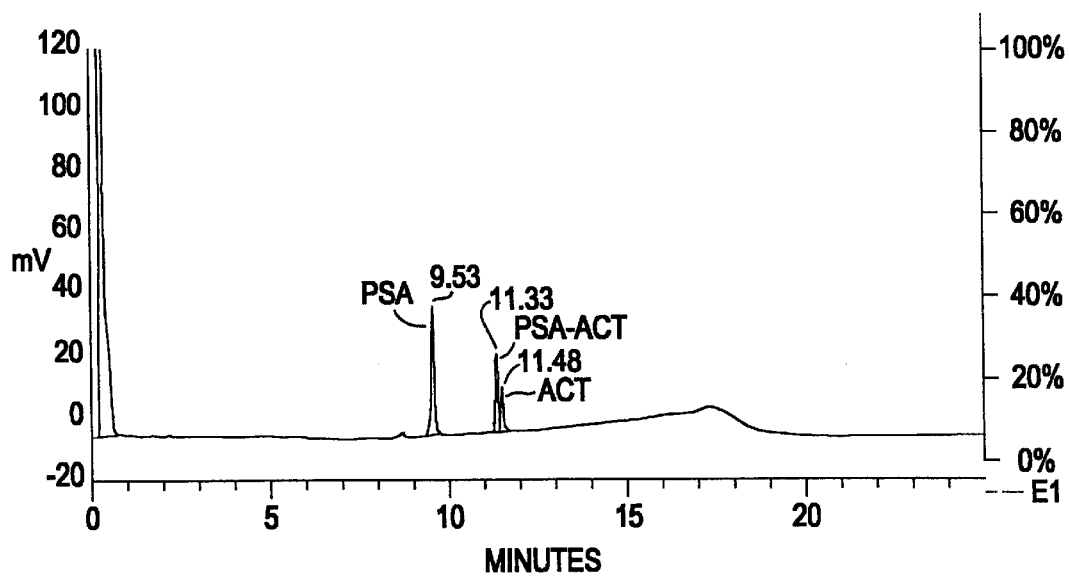
FIG. 2 shows an HPLC chromatogram of PSA-ACT after the cleavage in PSA and ACT with ethanolamine.

Cleavage of PSA-ACT in Malignant and Benign sera With a Final Concentration of 0.1 M Ethanolamine The $PSA_{total}$ detection is performed according to the procedure described in the package leaflet of the Enzymun-Test® PSA of Boehringer Mannheim GmbH, Germany (ident. No. 1 555 332). The $PSA_{free}$ concentration is determined according to the procedure described in the package leaflet of the Enzymun-Test® free PSA of Boehringer Mannheim GmbH, Germany (ident. No. 1 776 444). Both tests differ only in the specificity of the antibodies used. As far as the free PSA detection is concerned at least one antibody must be specific for free PSA and must therefore not bind to complex PSA whereas in the $PSA_{total}$ detection free as well as complex PSA must be recognized. For reasons of clarity all antibodies are however called "anti-PSA-antibodies" in the performance procedure. The test principle of both processes is a 1-step-sandwich ELISA based on the streptavidine technology. Together with an incubation solution containing biotinylated anti-PSA antibodies and anti-PSA antibodies labeled with peroxidase (POD) the sample is filled into a plastic tube coated with streptavidine. During the incubation the biotinylated antibody binds to the solid phase. The PSA present in the sample binds to the biotinylated antibody. The antibody labeled with POD binds to the PSA which is bound to the biotinylated antibody. The sandwich complexes bound to the solid phase are detected by an indicator reaction after a washing step. For this, a substrate-chromogen solution containing ABTS® (2,2'- azino-di-[3-ethyl-benzthiazoline-sulfonic acid (6)]-diammonium salt) and $H_2O_2$ is added to the preparation.

By the enzymatic activity of the peroxidase and depending on the amount of bound POD-labeled antibody a dye is built which can be detected photometrically.

The following measurements are performed with a series of human serum samples: At the beginning the $PSA_{free}$ concentration is determined in the first preparation according to the state of the art process without any sample pretreatment. In parallel, the $PSA_{total}$ concentration is determined according to the state of the art process, which means that for the detection antibodies binding PSA in a free and complex form are used. In the third preparation the sample is mixed with ethanolamine according to the invention (final concentration: 0.1 M) and after incubation for 24 hours at 25° C. the $PSA_{free}$ concentration is determined. The results of the malignant and benign sera are depicted in table 2.

TABLE 2

Comparison of the $PSA_{free}$ values after cleavage according to the invention with the $PSA_{total}$ values according to the state of the art process.

| Serum No. | $PSA_{free}$ Ng/ml 0 h | $PSA_{total}$ ng/ml 0 h | $PSA_{free\ after}$ cleavage ng/ml 24 h cleavage | Ratio $PSA_{free}$ 0 h/ $PSA_{total}$ 0 h | Ratio $PSA_{free}$ 0 h/ $PSA_{free}$ after 24 h of cleavage |
|---|---|---|---|---|---|
| a) Values of the malignant sera: | | | | | |
| 3 | 2.93 | 45.7 | 48 | 0.064 | 0.061 |
| 6 | 4.54 | 37.9 | 32.18 | 0.120 | 0.141 |
| 21 | 2.33 | 17.6 | 12.4 | 0.132 | 0.188 |
| 30 | 0.86 | 5.28 | 4.3 | 0.163 | 0.200 |
| 40 | 0.53 | 3.99 | 3.2 | 0.133 | 0.166 |
| 44 | 0.84 | 16.1 | 13.5 | 0.052 | 0.062 |
| 52 | 1.85 | 15.4 | 12.54 | 0.120 | 0.148 |
| 56 | 0.64 | 2.85 | 2.4 | 0.248 | 0.267 |
| 93 | 0.81 | 4.45 | 3.8 | 0.182 | 0.213 |
| 110 | 0.71 | 4.05 | 3.7 | 0.175 | 0.192 |
| 119 | 1.43 | 7.26 | 6.54 | 0.197 | 0.219 |
| 143 | 1.96 | 16.5 | 13.92 | 0.119 | 0.141 |
| 176 | 0.52 | 5.19 | 6.9 | 0.100 | 0.075 |
| 195 | 0.73 | 7.17 | 5.82 | 0.102 | 0.125 |

Correlation r between $PSA_{total}$ 0 h and $PSA_{free}$ after 24 h Cleavage: 0.985

| Serum No. | $PSA_{free}$ Ng/ml 0 h | $PSA_{total}$ ng/ml 0 h | $PSA_{free\ after}$ cleavage ng/ml 24 h cleavage | Ratio $PSA_{free}$ 0 h/ $PSA_{total}$ 0 h | Ratio $PSA_{free}$ 0 h/ $PSA_{free}$ after 24 h of cleavage |
|---|---|---|---|---|---|
| b) Values of the benign sera: | | | | | |
| 29 | 0.48 | 1.61 | 1.28 | 0.298 | 0.375 |
| 53 | 0.81 | 3.12 | 2.44 | 0.260 | 0.332 |
| 90 | 1.01 | 3.71 | 2.92 | 0.272 | 0.346 |
| 99 | 0.57 | 1.34 | 1.68 | 0.425 | 0.339 |
| 100 | 2.85 | 7.05 | 5.84 | 0.404 | 0.488 |
| 105 | 0.45 | 3.05 | 2.38 | 0.148 | 0.189 |
| 113 | 0.67 | 2.32 | 2.26 | 0.289 | 0.296 |
| 120 | 1.42 | 5.28 | 4.84 | 0.269 | 0.293 |
| 161 | 1.62 | 5.78 | 5.18 | 0.280 | 0.313 |
| 173 | 0.22 | 2.03 | 1.78 | 0.108 | 0.124 |
| 184 | 1.72 | 8.44 | 6.64 | 0.204 | 0.259 |
| 204 | 4.01 | 10.1 | 7.8 | 0.397 | 0.514 |
| 206 | 1.12 | 4.33 | 3.54 | 0.259 | 0.316 |

Correlation r between $PSA_{total}$ 0 h and $PSA_{free}$ after 24 h Cleavage: 0.99

It becomes clear that the PSAtotal concentration surprisingly corresponds to the concentration of free PSA which is determined after the cleavage of the PSA-serpin complexes according to the invention. The good correspondence of the ratios $PSA_{free}$ 0 h/$PSA_{total}$ after 0 h of cleavage and of $PSA_{free}$ 0 h/$PSA_{free}$ after 24 h of cleavage is proven by the correlation coefficients of each more than 0.98. This shows that with the help of according to the invention a procedure with one set of antibodies containing one antibody which specifically only binds to free PSA is sufficient to determine the $PSA_{free}$ $PSA_{total}$ as well as (by subtraction of the $PSA_{free}$ concentration from the $PSA_{total}$ concentration) the PSA-serpin concentration. In addition, the informative ratios total necessary for differentiation between malignant and benign prostate an be determined reliably.

What is claimed is:

1. A method for liberating prostate-specific antigen (PSA) from a PSA-serpin complex in a sample suspected of containing a PSA-serpin complex comprising incubating the sample with an amine containing nucleophile selected from the group consisting of ethanolamine, diethanolamine, ethylenediamine and tris(hydroxymethyl)aminomethane, thereby cleaving PSA from the PSA-serpin complex.

2. The method of claim 1, wherein the concentration of the an amine-containing nucleophile is between about 0.05 and 2 M.

3. The method of claim 1, wherein the sample is selected from the group consisting of serum, plasma, whole blood, semen and urine.

4. The method of claim 1, wherein the serpin is α-antichymotrypsin (ACT).

5. The method of claim 1, wherein the sample and amine-containing nucleophile are incubated with a buffer at a pH between about 9 and 11.

6. A method for determination of total PSA in a sample suspected of containing free PSA and a PSA-serpin complex comprising:

(a) forming a test mixture by combining the sample with an amine containing nucleophile selected from the group consisting of ethanolamine, diethanolamine, ethylenediamine and tris(hydroxymethyl)aminomethane, (b) incubating the test mixture, thereby cleaving PSA from the PSA-serpin complex, (c) adding to the test mixture an antibody specific for free PSA, and (d) determining the amount of antibody bound to the free PSA as a measure of total PSA in the sample.

7. The method of claim 6, wherein the concentration of the amine-containing nucleophile is between about 0.05 and 2 M.

8. The method of claim 6, wherein the sample is selected from the group consisting of serum, plasma, whole blood, semen and urine.

9. The method of claim 6, wherein the serpin is α-antichymotrypsin (ACT).

10. The method of claim 6, wherein the sample and amine-containing nucleophile are incubated with a buffer at a pH between about 9 and 11.

11. A method for determination of a ratio of free PSA to total PSA in a sample suspected of containing free PSA and PSA-serpin complexes comprising
(a) incubating a first part of said sample with an antibody which specifically binds to free PSA but not PSA-serpin complexes;
(b) determining the concentration of free PSA in the first part of the sample;
(c) incubating a second part of said sample with a reagent comprising an amine containing nucleophile selected from the group consisting of ethanolamine, diethanolamine, ethylenediamine and tris (hydroxyrnethyl)aminomethane;
(d) incubating the sample from step (c) with an antibody which specifically binds to free PSA but not PSA-serpin complexes;
(e) determining the concentration of free PSA in the second part of the sample, and thereby determining total PSA; and
(f) determining the ratio of free PSA to total PSA using the values obtained in steps (b) and (e).

12. The method of claim 11, wherein the the sample and amine-containing nucleophile are incubated with a buffer at a pH between about 9 and 11.

* * * * *